United States Patent [19]

Carvalho

[11] 4,103,147
[45] Jul. 25, 1978

[54] DEVICE FOR HEATING A BREAST PROSTHESIS

[76] Inventor: Birttie L. Carvalho, 15200 Wiley St., San Leandro, Calif. 94579

[21] Appl. No.: 745,043

[22] Filed: Nov. 26, 1976

[51] Int. Cl.² .............................................. H05B 1/00
[52] U.S. Cl. .................................. 219/524; 219/525; 219/527; 128/400; 99/390; 219/521
[58] Field of Search ............... 219/211, 212, 524, 525, 219/527, 528; 128/400, 402, 403; 3/36; 99/375, 390

[56] References Cited

U.S. PATENT DOCUMENTS

| 2,071,706 | 2/1937 | Reach | 128/403 X |
|---|---|---|---|
| 2,953,671 | 9/1960 | Allen et al. | 219/528 |
| 3,014,117 | 12/1961 | Madding | 219/525 X |
| 3,175,558 | 3/1965 | Caillouette et al. | 128/403 |
| 3,313,230 | 4/1967 | Simjian | 99/375 |
| 3,500,832 | 3/1970 | Nunnery | 128/402 X |
| 3,634,655 | 1/1971 | Jordan | 219/524 X |

Primary Examiner—Arthur T. Grimley
Assistant Examiner—Mark H. Paschall
Attorney, Agent, or Firm—William R. Piper

[57] ABSTRACT

A device for heating a breast prosthesis which comprises a base on which a liquid filled flexible bag is placed for supporting a breast prothesis. A hinged cover for the base that carries another liquid filled flexible bag on its in surface so that a closing of the cover will cause the under surface of the bag to contact with and conform to the irregular contour of the upper surface of the breast prosthesis. An electric heating element is submerged in the liquid in each bag and a switch and thermostat for the heating elements controls the degreee of heat applied to the breast prosthesis.

1 Claim, 3 Drawing Figures

DEVICE FOR HEATING A BREAST PROSTHESIS

SUMMARY OF THE INVENTION

If a breast prosthesis is permitted to return to room temperature when it is not worn, then when it is worn the persons body temperature will be at a much higher degree of heat than the prosthesis and the body becomes chilled in the area where contact is made. It requires considerable time before the temperature of the prosthesis reaches that of the body and the person is under extreme discomfort during this period of time. In order to overcome this, I have invented a device for maintaining the prosthesis at body temperature while it is not being worn.

The shape of a breast prosthesis varies for each person who wears one. I have therefore provided my device with a base that supports a flexible water bag whose upper surface conforms to the irregular undulating undersurface of the prosthesis. In addition the hinged cover of my device also carries an upper flexible water bag whose undersurface conforms to the irregular upper surface of the breast prosthesis so that contact will be made throughout the entire area when the cover is closed. An electric heating element is submerged in the liquid in each bag and a thermostat controls the temperature so as to maintain the desired degree of heat on the breast prosthesis to keep it substantially at the body temperature of the person who is to wear it.

DESCRIPTION OF THE PREFERRED EMBODIMENT

Figure 2:
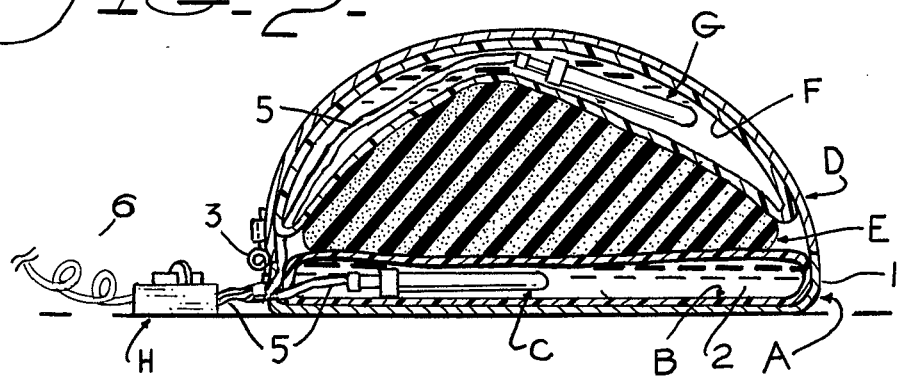
FIG. 2 is a vertical longitudinal section through the device and is taken along the line 2—2 of FIG. 1.
Figure 3:
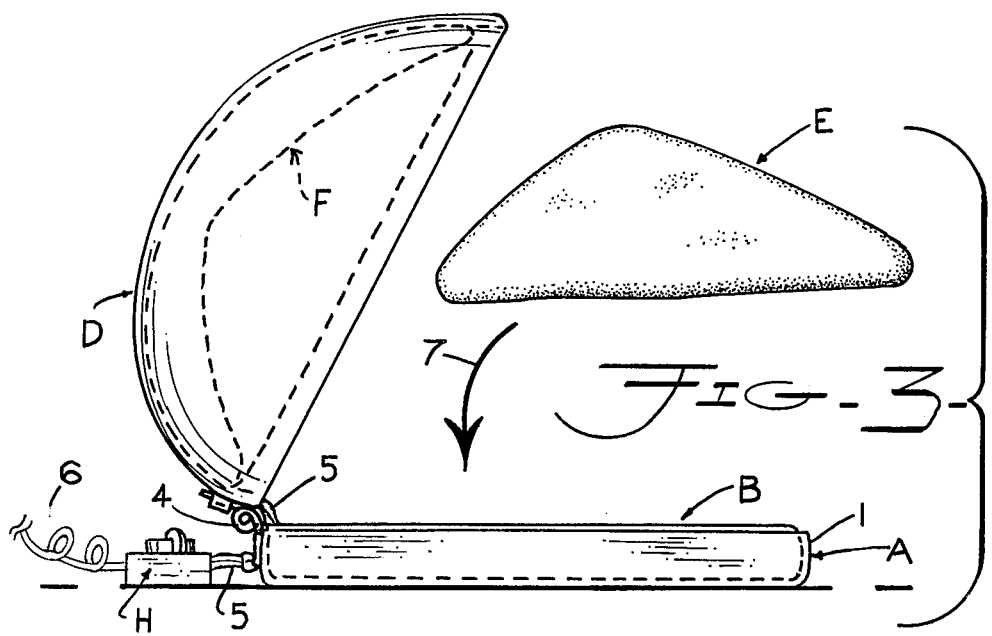
FIG. 3 is a side elevation of the device showing the cover in open position and the device ready to receive the breast prosthesis.

In carrying out my invention I provide a base, indicated at A in FIGS. 2 and 3. The base is preferably made from a thermally non-conductive material and has an upturned flange 1 encircling the base perimeter to form a cavity that receives a flexible bag B, filled with liquid such as water. The bag B, is made from a material that will transmit heat, such as rubber or plastic. FIG. 2 shows an electric heating element C, submerged in the liquid 2 in the bag B.

Figure 1:
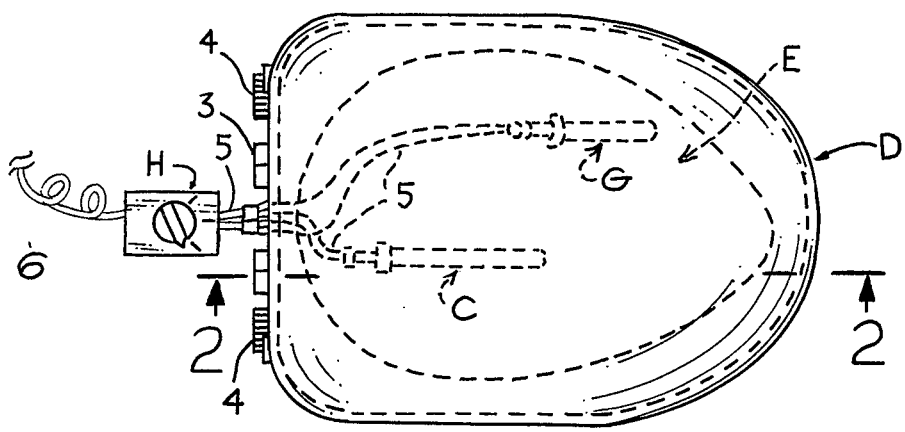
FIG. 1 is a top plan view of the breast prothesis warming device.

A cover D is preferably made from a thermally non-conductive material and is hinged at 3 to the base A, and torsional springs 4 are used to counterbalance the weight of the cover, see FIGS. 1 and 3. The shape of a breast prosthesis varies according to the individual who wears it. I have shown in FIG. 3 a side view of the prosthesis E while FIG. 1 illustrates a top plan view by dotted lines and FIG. 2 is a vertical and longitudinal section through the prosthesis.

The cover D has a large cavity for receiving the upper portion of the breast prosthesis E. I secure a second or upper flexible water bag F to the interior of the cover so that when the cover is in closed position, as shown in FIG. 2, the undersurface of the flexible water bag F will contact and conform to the irregular top surface of the prosthesis. The bag F is made from a material that will transmit heat, such as rubber or plastic. In this way the entire lower surface will be contacted by the lower water bag B while the entire upper surface will be contacted by the top water bag F. The flexible bags B and F are filled with a liquid and hermetically sealed.

An electric heating element G, is immersed in the liquid in the upper flexible bag F, see FIG. 2, for maintaining the liquid at a temperature which in turn will keep the prosthesis substantially at the temperature of the wearer's body. In FIGS. 1 and 2 I show electric wiring 5 connecting the heating elements C and G, to a standard rheostat control H which also includes an ON/OFF electric switch. The control for the rheostat may be set to the desired body temperature. A wire 6 connects the thermostat and switch to an electric outlet, not shown.

OPERATION

From the foregoing description of the various parts of the device, the operation may be readily understood. FIG. 3 shows the breast prosthesis being placed on the lower flexible water bag B, as indicated by the arrow 7. The entire under surface of the prosthesis will be intimately contacted by the upper flexible surface of the water bag so as to uniformly heat the underside of the prosthesis.

It is to be understood that although I show a prosthesis representing and shaped as a single breast, the device can readily be enlarged and the two water bags shaped for receiving a double prosthesis representing a double breast. The cover D will have considerable weight added to it when the upper flexible bag F, is filled with a liquid. The bag may be filled with water or any other kind of fluid that may be heated by the heating element G and transmit this heat uniformly over the upper surface of the breast prosthesis. The torsional springs 4 are for the purpose of substantially counterbalancing the weight of the cover D, and its upper flexible bag F.

When the cover D encloses the prosthesis E, the two flexible bags B and F will contact its entire outer surface. The electric current may be turned on and the desired temperature set by the thermostat. This will cause the heating elements C and G to heat the liquid in the two bags B and F to maintain the prosthesis at a temperature of a person's body who is to wear the prosthesis. The person therefore does not have to undergo the extremely uncomfortable experience of warming the large contacting area of the prosthesis to a body temperature. The device is simple in construction and operation and will fulfill a real need of maintaining a breast prosthesis at a person's body temperature while it is not being worn so that there will be no necessity of raising the temperature of the prosthesis while it is being worn by the one using it.

I claim:

1. A breast prosthesis heater comprising:
    (a) a base;
    (b) a first flexible waterproof thermally conductive and electrically non-conductive material sealed and liquid containing bag supported by said base and adapted to support a breast prosthesis, the upper surface of said bag conforming to the under surface of the prosthesis so as to have uniform contact therewith;
    (c) a dome-shaped cover for said base and being hingedly connected thereto;
    (d) a second flexible, waterproof, thermally conductive and electrically non-conductive material, sealed and liquid containing bag secured to the inner surface of said dome-shaped cover, the undersurface of said second bag conforming to the irregular upper surface of the prosthesis when the prosthesis rests on said first bag and said cover is in closed position; whereby substantially the entire exterior surface of the prosthesis is uniformly contacted by both bags;

(e) an electric heating element submerged in the liquid in each bag for heating said liquids; and (f) an electric insulated cord interconnecting said heating elements with an electric outlet and having temperature control means for controlling the heat delivered by said heating elements to maintain the breast prothesis at the temperature of the human body.

* * * * *